United States Patent [19]

Suresh et al.

[11] Patent Number: 5,171,876
[45] Date of Patent: Dec. 15, 1992

[54] METHOD FOR AMMOXIDATION OF PARAFFINS

[75] Inventors: Dev D. Suresh, Hudson; Michael J. Seeley, Twinsburg; Jeanette R. Nappier, Parma; Maria S. Friedrich, Lyndhurst, all of Ohio

[73] Assignee: The Standard Oil Company, Cleveland, Ohio

[21] Appl. No.: 760,285

[22] Filed: Sep. 16, 1991

[51] Int. Cl.$^5$ .......................................... C07C 253/24
[52] U.S. Cl. .................................... 558/319; 502/215; 502/209; 502/211
[58] Field of Search ........................................ 558/319

[56] References Cited

U.S. PATENT DOCUMENTS

| | | | |
|---|---|---|---|
| 4,309,361 | 1/1982 | Suresh et al. | 558/319 X |
| 4,316,855 | 2/1982 | Grasselli et al. | 568/477 X |
| 4,436,671 | 3/1984 | Furuoya et al. | 558/319 |
| 4,760,159 | 7/1988 | Suresh et al. | 558/319 |
| 4,871,706 | 10/1989 | Brazdil, Jr. et al. | 558/319 X |
| 4,874,738 | 10/1989 | Brazdil, Jr. et al. | 558/319 X |
| 4,883,895 | 11/1989 | Brazdil, Jr. et al. | 558/319 |
| 4,883,896 | 11/1989 | Glaeser et al. | 558/319 |
| 4,888,438 | 12/1989 | Glaeser et al. | 558/319 |
| 5,008,427 | 4/1991 | Brazdil, Jr. et al. | 558/319 |
| 5,049,692 | 9/1991 | Hatano et al. | 558/319 |

*Primary Examiner*—Joseph Paul Brust
*Attorney, Agent, or Firm*—C. S. Lynch; M. F. Esposito; L. W. Evans

[57] ABSTRACT

Disclosed is a process for making an α, β-unsaturated mononitrile by the catalytic reaction of a paraffin containing 3-5 carbon atoms with molecular oxygen and ammonia by catalytic contact of the foregoing reactants in a reaction zone with a metal oxide catalyst containing the elements indicated by the empirical formula, $$Cr_aMo_bTe_cM_dO_x \qquad \text{(formula 1)}$$

where
M = one or more of Mg, Ni, Sb, Ti, La, P, Ce, Fe, Nb, W, V, and Cu, each of a, b & c is 0.1 to 10
d is zero to 10
a+b+c>1.5d, and
x is determined by the valence requirements of the other elements present, and wherein the reactants fed to the reaction zone contain a mole ratio of said paraffin:NH$_3$ in the range from 2.5 to 16 and a mole ratio of said paraffin:O$_2$ in the range from 1 to 10.

1 Claim, No Drawings

METHOD FOR AMMOXIDATION OF PARAFFINS

This invention relates to an improved process for the catalytic ammoxidation of paraffins containing from 3 to 5 carbon atoms to α, β-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Early attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated mononitriles and the corresponding mono-olefins.

Still another object is to provide an improved catalyst for making unsaturated mononitriles from lower paraffins.

Other objects, as well as aspects, features and advantages, of the present invention will become apparent from a study of the accompanying disclosure and the claims.

These and other objects are achieved by the present invention according to one aspect of which there is provided a process for making an α, β-unsaturated mononitrile by the catalytic reaction of a paraffin containing 3-5 carbon atoms with molecular oxygen and ammonia by catalytic contact of the foregoing reactants in a reaction zone with a metal oxide catalyst containing the elements and proportions indicated by the empirical formula,

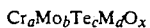  (formula 1)

where

M = one or more of Mg, Ni, Sb, Ti, La, P, Ce, Fe, Nb, W, V, and Cu, each of a, b & c is 0.1 to 10 d is zero to 10 a+b+c>1.5 d, and x is determined by the valence requirements of the other elements present, and wherein the reactants fed to the reaction zone contain a mole ratio of said paraffin:$NH_3$ in the range from 2.5 to 16 and a mole ratio of said paraffin:$O_2$ in the range from 1 to 10.

In the practice of the process of the invention the catalyst can be used as such, but it usually contains an inorganic oxide support or diluent present as an integral part of the catalyst. Such diluents are well known in the catalyst art and include silica, alumina, alundum, zirconia, etc. We have found a silica-alumina support/diluent containing $SiO_2$:$Al_2O_3$ weight ratio in the range from 1:10 to 10:1, particularly from 4:6 to 6:4 to be especially useful. The support when present is not an oxide of an element of the foregoing empirical formula.

U.S. application Ser. No. 620,814, filed Dec. 3, 1990, now U.S. Pat. No. 5,079,207, discloses ammoxidation of paraffins with a catalyst containg V, (Te or Bi), Sn, Sb and Cu that can optionally also contain Mo and Cr among others, but the ratios of components are completely different than in the present claims.

A Derwent abstract of European application EP-No.318295-A discloses a catalyst having Mo, V, Te and Nb in oxide form for ammoxidation of an alkane, but this catalyst contains no chromium.

U.S. Pat. Nos. 4,316,855 and 4,532,083 disclose ammoxidation of olefins but not paraffins in the presence of a catalyst containing Sb, Sn, and Te and that can contain Cu, V, W, Mo, Bi, Ti, Ge, La, Cr, Mn, Mg, Ca, Co, Ni, Nb, Ta, Ag, Zn, Cd, K, Cs, B, P, and Eu.

The process of the present invention requires no halogen or halogen compounds and no sulfur or sulfur compounds in any form in the reaction zone, from either the feed to the reaction zone or in the catalyst composition.

In the catalyst compositions of the invention the empirical formula denotes the atomic ratios of the listed elements and does not, of course, connote any particular chemical compound, nor indicate whether the elements are present as a mixture of individual oxides or as a complex oxide or oxides, or what separate crystalline phases or solid solutions may be present. However, the catalyst contains the elements and proportions indicated by the foregoing formula. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports or carriers in the catalyst art. Such designations, however, do not mean that the element involved is actually present as a simple oxide. Indeed, such elements may at times be present as a complex oxide with one, more than one, or all of the elements in the foregoing empirical formula, which complex oxides form during the process for preparing the catalyst composition.

In the ammoxidation of the present invention, the reaction is carried out in the gas phase by contacting a mixture containing the paraffin, ammonia and molecular oxygen, and diluent, if any, conveniently in a fixed bed of the catalyst, or a gravity flowing bed, a fluidized bed or a fast transport reactor mode.

The mole ratio of $O_2$ to $NH_3$ fed to the reaction zone is usually in the range from 1-10 (more often 1-5), and the mole ratio of gaseous diluent (other than $C_3$ to $C_5$ paraffin) to paraffin is usually in the range from zero-20 (more often zero-12); of course, even higher molar ratios, say up to 50 mols diluent to 1 mols paraffin, can be used but are usually uneconomical.

In the present process, when applied to propane ammoxidation, a small amount of propylene is produced in relation to the unreacted propane in the effluent. Thus the propane effluent containing propylene in the amount of up to 8 mole percent, but usually no more than 6 mole percent, of the amount of propane plus propylene can comprise substrate feed to the present process.

And in general the $C_3$ to $C_5$ alkane feed to the reaction zone of the process of the present invention can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. However, larger amounts of $C_3$ to $C_5$ olefins may be present in the substrate paraffin feed, but the usual proportions are as stated, and the usual olefin is that corresponding to the particular paraffin fed to the reaction zone of the present ammoxidation process.

Examples of diluents useful in the reaction zone are $N_2$, He, $CO_2$, CO, $H_2O$ and Ar. The unreacted excess paraffin, such as propane, over the stoichiometric amount of $O_2$ and $NH_3$ acts, of course, as a diluent or further diluent. The excess paraffin as recited in the claims is an important feature of the invention.

The reaction temperature range can vary from 350° to 700°, but is usually 440° to 550° C. The latter temperature range is especially useful in the case of propane ammoxidation to acrylonitrile.

The average contact time can often be from 0.01 to 10 seconds, but is usually from 0.02 to 10 seconds, more usually from 0.1 to 8 seconds.

The pressure of the reaction usually ranges from 1 to 45 psig. Most often, pressure is somewhat above atmospheric, i.e. 1 to 20 psi.

In any event, the pressure, temperature and contact times are not the essence of the invention and can be outside these ranges. The most advantageous combination of these conditions for a given desired result from a given feed can be determined by routine experimentation.

The nitrile products of the present process contain one C to C double bond and one nitrile group. The desired olefin products contain one double bond and the same number of C atoms as the paraffin feed.

The catalysts of the inventions contain the elements indicated by the empirical formula 1 in the relative atomic proportions indicated by such formula, as already noted. They can be used in unsupported form or with suitable carriers such as silica, alumina, zirconia or mixtures thereof. In specific examples herein where $SiO_2$, alumina, or silica-alumina are present, they are such carriers.

The following examples of the catalysts and of the ammoxidation runs of the invention are exemplary and should not be taken as in any way limiting.

CATALYST EXAMPLE 1

7.83 g of $(NH_4)_6Mo_7O_{24}.4H_2O$ were dissolved in water. A second solution was made by adding a water solution of 5.69 g of $Mg(NO_3)_2.6H_2O$ with a water solution of 8.87 g of $Cr(NO_3)_3.9H_2O$. The two separate solutions were then mixed. To the resulting solution was added an aqueous slurry of 3.54 g of $TeO_2$ Then 15.62 g of a 40 wt. % $SiO_2$ sol were added, followed by 31.25 g of a 20 wt. % $Al_2O_3$ sol. The resulting slurry was concentrated on a hotplate and then dried at 120° C. The solid was calcined at 290° C. for 3 hrs., then 425° C. for 3 hrs. It was ground and screened to 20/35 mesh and then calcined at 610° C. for 3 hrs.

CATALYST EXAMPLE 2

To a solution of 10.42 g of $(NH_4)_6Mo_7O_{24}.4H_2O$ in 200 ml of warm water were added 0.94 g of $TeO_2$ slurried in water, followed by 7.87 g of $Cr(NO_3)_3.9H_2O$ dissolved in 100 ml of water, 13.42 g of a 11.7 wt. % $TiO_2$ sol, 15.62 g of a 40 wt. % $SiO_2$ sol and 31.25 g of a 20 wt. % $Al_2O_3$ sol. The solid was calcined at 290° C. for 3 hrs., then 425° C. for 3 hrs. It was ground and screened to 20/35 mesh and then calcined at 610° C. for 3 hrs.

CATALYST EXAMPLE 3

To a water solution of 11.15 g of $(NH_4)_6Mo_7O_{24}.4H_2O$ in 200 mls of warm water was added a water slurry of 1.01 g of $TeO_2$, followed by 12.64 g of $Cr(NO_3)_3.9H_2O$ dissolved in 100 ml of water. To this slurry was added 15.62 g of a 40% $SiO_2$ sol and 31.25 g of a 20% $Al_2O_3$ sol. Drying and heat treatment was as in Catalyst Example 1, including the grinding and screening.

CATALYST EXAMPLE 4

To a solution of 11.21 g of $(NH_4)_6Mo_7O_{24}.4H_2O$ in 200 ml of warm water were added 14.27 g of a 12 wt. % $Sb_2O_5$ sol, followed by a water sol of 0.84 g of $TeO_2$ and an aqueous solution of 4.23 g of $Cr(NO_3)_3.9H_2O$, 15.62 g of a 40 wt. % $SiO_2$ sol and 31.25 g of a 20 wt. % $Al_2O_3$ sol. Subsequent treatment was the same as for Catalyst Example 1, except that the final 3 hours of calcination was at 650° C.

CATALYST EXAMPLE 5

To 6.45 g of $(NH_4)_6Mo_7O_{24}.4H_2O$ which had been dissolved in 200 ml of warm water was added a total of 2.99 g of Te metal in small portions, alternating with the dropwise addition of $H_2O_2$, until all of the Te metal was dissolved (yellow solution, using about 18 cc of 30% $H_2O_2$). 15.65 g of $Cr(NO_3)_3.9H_2O$ and 3.34 g of $Mg(NO_3)_2.6H_2O$ were dissolved separately in water, then combined and added to the yellow solution, followed by the addition of 15.62 g of a 40 wt. % $SiO_2$ sol and 31.25 g of a 20 wt. % $Al_2O_3$ sol. Further processing was the same as in Catalyst Example 1.

CATALYST EXAMPLE 6

To 12.20 g of $(NH_4)_6Mo_7O_{24}.4H_2O$ which had been dissolved in 200 ml of warm water was added a total of 8.82 g of Te metal in small portions, alternating with the dropwise addition of $H_2O_2$, until all of the Te metal was dissolved (yellow solution, using about 40 cc of 30% $H_2O_2$). 13.83 g of $Cr(NO_3)_3.9H_2O$ and 8.86 g of $Mg(NO_3)_2.6H_2O$ were dissolved separately in water, then combined and added to the yellow solution, followed by the addition of 31.25 g of a 40 wt. % $SiO_2$ sol and 62.50 g of a 20 wt. % $Al_2O_3$ sol. Further processing was the same as in Catalyst Example 1.

In the following ammoxidation examples, the catalyst is in a tubular ⅜ inch I.D. titanium fixed bed reactor. Pressure is slightly above atmospheric. The reactor is equipped with a preheat leg and is immersed in a temperature controlled molten salt bath. The feed is fed to the catalyst for at least one hour before collection of product; the runs of each example last 30–60 minutes during which the product is collected for analysis.

EXAMPLE I

In this example, the catalyst was Catalyst 1, the reaction temperature was 470° C., the contact time was 2.6 seconds and the mole ratios in the feed to the reactor were 5 propane/0.85 $NH_3$/2 $O_2$/1 $H_2O$ The conversion of the propane was 11.1%, and the yield and selectivity to acrylonitrile were 6.2% and 55.6%, while the yield and selectively to propylene were 0.81% and 7.3%.

EXAMPLE II

In this example, the catalyst was Catalyst 2, the reaction temperature was 490° C., the contact time was 0.5 seconds and the mole ratios in the feed to the reactor were 5 propane/1 $NH_3$/2 $O_2$/1 $H_2O$ The conversion of the propane was 16.1%, and the yield and selectivity to acrylonitrile were 7.0% and 43.5%, while the yield and selectively to propylene were 3.5% and 21.6%.

EXAMPLE III

In this example, the catalyst was Catalyst 6, the reaction temperature was 486° C., the contact time was 2.6 seconds and the mole ratios in the feed to the reactor were 5 propane/1 $NH_3$/3 $O_2$/1 $H_2O$ The conversion of the propane was 15.5%, and the yield and selectivity to acrylonitrile were 8.3% and 53.9%, while the yield and selectively to propylene were 0.77% and 5.0%.

EXAMPLE IV

In this example, the catalyst was Catalyst 4, the reaction temperature was 470° C., the contact time was 2.8 seconds and the mole ratios in the feed to the reactor were 3 propane/1 $NH_3$/2 $O_2$/1 $H_2O$/2 $N_2$ The conversion of the propane was 16.7%, and the yield and selectivity to acrylonitrile were 8.5% and 51.0%, while the yield and selectively to propylene were 1.5% and 8.9%.

EXAMPLE V

In this example, the catalyst was Catalyst 5, the reaction temperature was 470° C., the contact time was 0.9 seconds and the mole ratios in the feed to the reactor were 5 propane/0.85 $NH_3$/2 $O_2$/1 $H_2O$ The conversion of the propane was 13.7%, and the yield and selectivity to acrylonitrile were 7.3% and 52.8%, while the yield and selectively to propylene were 1.1% and 10.2%.

EXAMPLE VI

In this example, the catalyst was Catalyst 3, the reaction temperature was 480° C., the contact time was 1.5 seconds and the mole ratios in the feed to the reactor were 3 propane/1 $NH_3$/2 $O_2$/1 $H_2O$/2 $N_2$ The conversion of the propane was 18.9%, and the yield and selectivity to acrylonitrile were 8.3% and 46.0%, while the yield and selectively to propylene were 2.4% and 13.4%.

As will be evident to those skilled in the art, various modifications of this invention can be made or followed in the light of the foregoing disclosure and discussion without departure from the spirit and scope of the disclosure or from the scope of the claims.

We claim:

1. A process for making an $\alpha$, $\beta$-unsaturated mononitrile by the catalytic reaction of a paraffin containing 3-5 carbon atoms with molecular oxygen and ammonia by catalytic contact of the foregoing reactants in a reaction zone with a metal oxide catalyst containing the elements and proportions indicated by the empirical formula, $$Cr_aMo_bTe_cM_dO_x \qquad \text{(formula 1)}$$

where
M = one or more of Mg, Ni, Sb, Ti, La, P, Ce, Fe, Nb, W, V, and Cu, each of a, b & c is 0.1 to 10
d is zero to 10
a+b+c > 1.5 d, and
x is determined by the valence requirements of the other elements present, and wherein the reactants fed to the reaction zone contain a mole ratio of said paraffin:$NH_3$ in the range from 2.5 to 16 and a mole ratio of said paraffin:$O_2$ in the range from 1 to 10.

* * * * *